United States Patent [19]

Dam

[11] Patent Number: 4,607,520

[45] Date of Patent: Aug. 26, 1986

[54] METHOD AND APPARATUS FOR DETECTING DISCONTINUITIES IN A FLUID STREAM

[75] Inventor: Naim Dam, Oakland Gardens, N.Y.

[73] Assignee: Introtek Corporation, Deer Park, N.Y.

[21] Appl. No.: 569,389

[22] Filed: Jan. 9, 1984

[51] Int. Cl.[4] .......................................... G01N 29/02
[52] U.S. Cl. ...................................... 73/19; 73/61 R; 73/861.28; 73/861.41; 73/DIG. 4
[58] Field of Search ............... 73/19, 24, 28, 53, 61 R, 73/61.1 R, 703, 861.18, 861.19, 861.27, 861.28, 861.41, DIG. 4

[56] References Cited

U.S. PATENT DOCUMENTS

| | | | |
|---|---|---|---|
| 2,949,769 | 8/1960 | Heller | 73/53 X |
| 2,966,056 | 12/1960 | Heller | 73/53 X |
| 2,966,057 | 12/1960 | Heller | 73/53 X |
| 3,392,574 | 7/1968 | Lemon et al. | 73/53 |
| 3,623,363 | 11/1971 | Dory | 73/61.1 R X |
| 3,710,621 | 1/1973 | Asada | 73/861.28 |
| 3,859,846 | 1/1975 | Asada et al. | 73/61.1 R X |
| 3,881,353 | 5/1975 | Fathauer | 73/861.41 |
| 3,914,984 | 10/1975 | Wade | 73/61.1 R X |
| 3,921,622 | 11/1975 | Cole | 73/61 R X |
| 3,977,252 | 8/1976 | Krylova et al. | 73/703 |
| 4,015,464 | 4/1977 | Miller et al. | 73/61 R |
| 4,015,470 | 4/1977 | Morrison | 73/53 X |
| 4,022,058 | 5/1977 | Brown | 73/861.28 |
| 4,065,958 | 1/1978 | Krylova et al. | 73/53 |
| 4,095,457 | 6/1978 | Koda et al. | 73/53 |
| 4,138,879 | 2/1979 | Liebermann | 73/61 R X |
| 4,235,095 | 11/1980 | Liebermann | 73/61 R X |
| 4,339,944 | 7/1982 | Abts et al. | 73/61 R X |
| 4,345,479 | 8/1982 | Loveland | 73/861.28 |
| 4,347,747 | 9/1982 | Srinivasan | 73/861.18 |
| 4,446,744 | 5/1984 | Bearcroft | 73/861.28 |
| 4,468,971 | 9/1984 | Herzl et al. | 73/861.28 |
| 4,478,072 | 10/1984 | Brown | 73/61 R |
| 4,480,485 | 11/1984 | Bradshaw et al. | 73/861.28 |

FOREIGN PATENT DOCUMENTS 968,561  9/1964  United Kingdom .................. 73/53

Primary Examiner—Robert Spitzer
Attorney, Agent, or Firm—Darby & Darby

[57] ABSTRACT

Method and apparatus for detecting discontinuities, such as bubbled, in a fluid stream, in which a tube is placed between a transducer transmitting successive bursts of ultrasonic energy and for receiving the bursts. The receiving transducer is connected to a signal processing circuit which keeps an indicator in a first state when signals are received corresponding to the presence of a fluid and in a second state when the bursts of energy are modified by the discontinuity.

15 Claims, 3 Drawing Figures

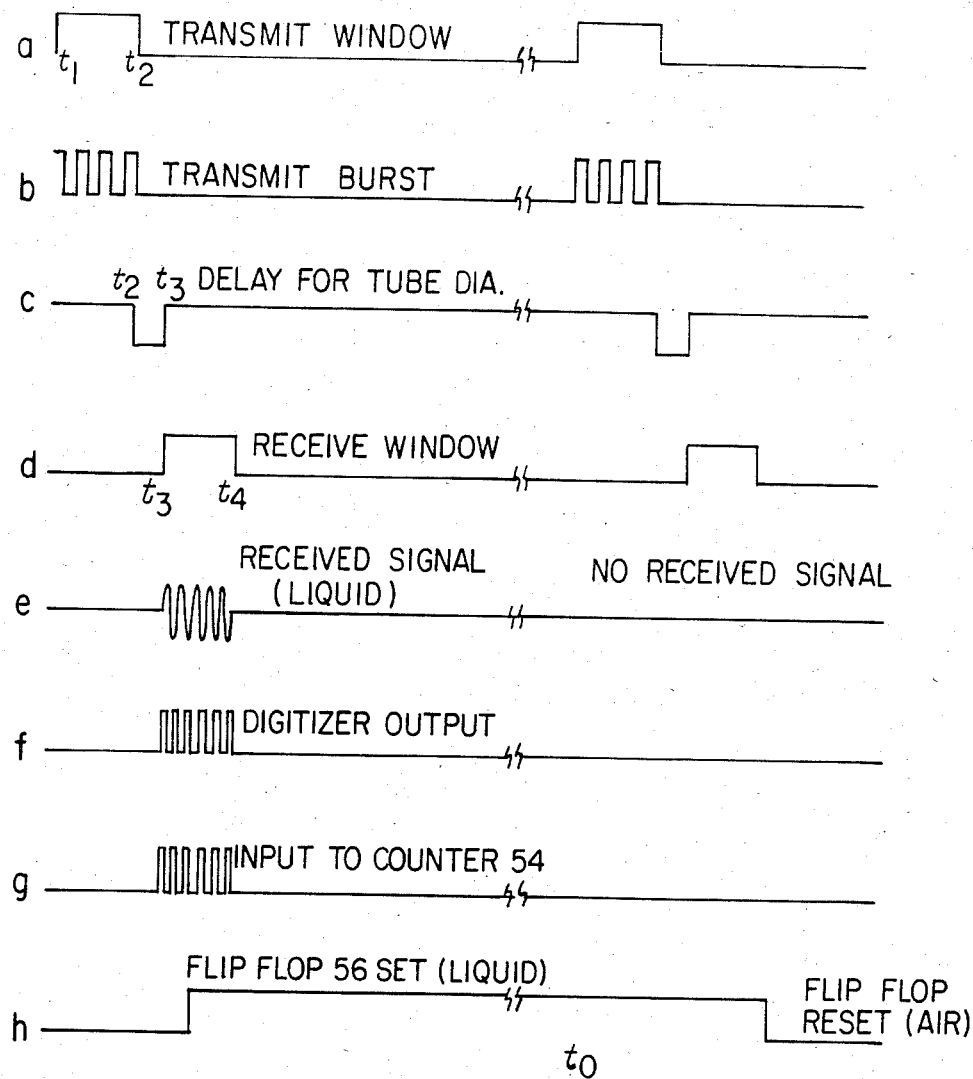

METHOD AND APPARATUS FOR DETECTING DISCONTINUITIES IN A FLUID STREAM

The present invention relates to a method and apparatus for detecting discontinuities, such as bubbles, in a fluid flow utilizing ultrasonic energy.

Various arrangements have been proposed for detecting bubbles in a flow of liquid, particularly where the liquid is in a tubing which is either rigid or compressible. Some of the uses for such a bubble detector would be, for example, in detecting air bubbles in body fluids, such as blood, which are being transmitted from one place to another either with the patient in the transmittal loop or from one type of a machine, such as blood processing machine, to another such machine.

Various arrangements previously have been provided for making such detection. Included among these are, for example, U.S. Pat. No. 3,921,622 to Cole in which bubble detection is accomplished by detecting a change in amplitude of a received ultrasonic pulse versus the amplitude of a pulse which passes through air. Another U.S. Pat. No. is 3,974,681 to Namery which uses an amplitude measuring technique, with the components being optimized at particular resonant frequencies of the system.

In the system disclosed in U.S. Pat. No. 4,122,713, to Stasz, a doppler and backscatter technique is used. In Liebermann U.S. Pat. No. 4,138,879, bubbles are detected by transmitting ultrasonic signals through a tube from one transducer to another with an amplifier being maintained in a marginally oscillatory condition. The detection of the bubbles changes the operating state of the system, and the change of state is detected.

In Bilstad U.S. Pat. No. 4,341,116 an arrangement is used in which amplitude levels are detected by a comparator. Liebermann U.S. Pat. No. 4,392,374 uses an adjustable bandpass technique while Abts U.S. Pat. No. 4,237,720 utilizes an ultrasonic transducer as a focusing lens. Another patent of interest is U.S. Pat. No. 4,068,521 to Cosentino et al, in which both continuous wave and pulses of ultrasonic energy can be used. The reception or non-reception of the energy is used on an amplitude basis.

Some of the bubble detectors described, particularly those detecting on the basis of amplitude of received signal, have a problem in detecting the bubbles caused by the size of the tube in which the fluid flows, the aging of the tube, which reduces its wall thickness and its flexibility, tube wall thickness and also with respect to bubble size. All of these problems give rise to variations in amplitude of the detected received signal. For a constant gain and constant threshold circuit, reliable detection of an air bubble becomes a serious problem.

The present invention relates to a novel method and apparatus for detecting bubbles in a stream of liquid flowing in a tube by the use of pulsed ultrasonic energy. In accordance with the invention, bursts of pulses of ultrasonic energy are transmitted from a transmitting transducer to a receiving transducer. A tube in which the fluid, perhaps containing bubbles, flows is held between the two transducers. The time of arrival of the signals is measured and signal processing is performed to insure reliable detection. If there are bubbles in the line, no signals are detected and this state is also detected.

It is therefore an object of the present invention to provide a novel bubble detector and method of bubble detection.

A further object is to provide a method and apparatus for detecting bubbles in which pulsed ultrasonic energy is used.

Still another object is to provide a bubble detector in which bursts of ultrasonic energy are used and the received bursts are signal processed.

Other objects and advantages of the present invention will become more apparent upon reference to the following specification and annexed drawings in which:

FIG. 3 shows a timing diagram for the unit.

Figure 1:
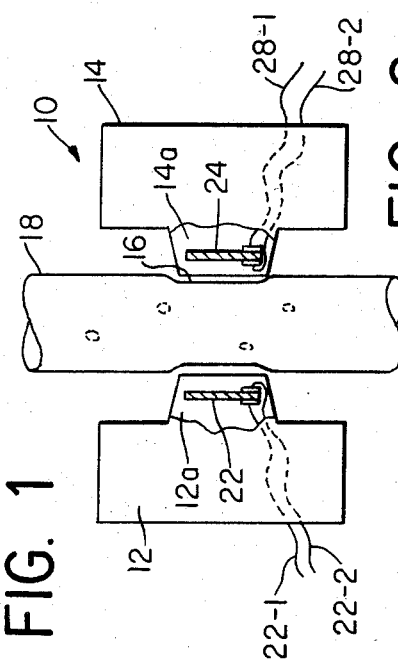
FIG. 1 is an elevational view of the sensing head for the tubing shown partially broken away.

FIG. 1 shows a sensing head 10 having two sections 12 and 14. Each section has a respective projection 12a, 14a forming a space 16 within which a tube 18, for example of compressible plastic material, is placed. A rigid chamber of plastic or glass or other material can be used, if desired. The space between the projections 12a, 14b is selected so that there will be a tight fit for the tube and preferably the portion of the tube held between the two projections is flattened. By using the arrangement with a compressible tube, the use of ultrasonic energy coupling compound, e.g. silicone grease, can be avoided. If the tubing 18 is of glass or other noncompressible material, then the opening 16 is sized to provide a firm fit and coupling compound used.

Each of the sections 12, 14 has a respective ultrasonic transducer 22, 24 embedded therein. the transducers can be for example, of any suitable piezoelectric material as is well known in the art, for example, PZT. As is conventional, each transducer 22,24 has a electrode on each face and a lead is connected thereto, the leads being designated 26-1, 26-2 and 28-1, 28-2. The leads provide energy to or convey energy from the respectively connected transducer. The sensing head sections are preferably molded from a suitable material, for example, an epoxy. The transducers elements and the wires are also molded within the head sections. The sections of the sensing head can be molded as a one-piece unit with a common back support or as separate pieces and then mounted to a common support.

In describing the invention, transducer 22 is the transmitter and transducer 24 is the receiver. That is, transducer 22 receives bursts of electrical energy and converts them into ultrasonic energy which is transmitted through the tube 18 toward the receiving transducer 24. If there is liquid in the tube, the energy is transmitted through the tube and received by the receiving transducer 24 which converts the ultrasonic energy into electrical energy which can be detected by a suitable electronic circuitry. If there is a discontinuity in the fluid stream in the tube, for example, an air bubble, then there is no signal received. For ease of description, the invention is described with respect to air bubbles in the fluid stream.

The size of the transducers determine the size of the bubble which can be reliably detected. That is, the surface area of each piezoelectric element is made slightly larger than the minimum size bubble to be detected. Generally, the diameter of the bubble to be detected is about one half the wavelength of the crystal resonant frequency. The resonant frequency is a function of the active surface area of the element. If there is a bubble in the tube which is equal to or larger than the size of the transducer, then there will be no signal received by the receiving transducer 24. It should be understood that the bursts of ultrasonic energy are transmitted at a rate which is substantially greater than the flow rate of the bubbles in the tube so that any stoppage of transmission of the energy through the tube, caused by the presence of an air bubble, is reliably detected.

Figure 2:
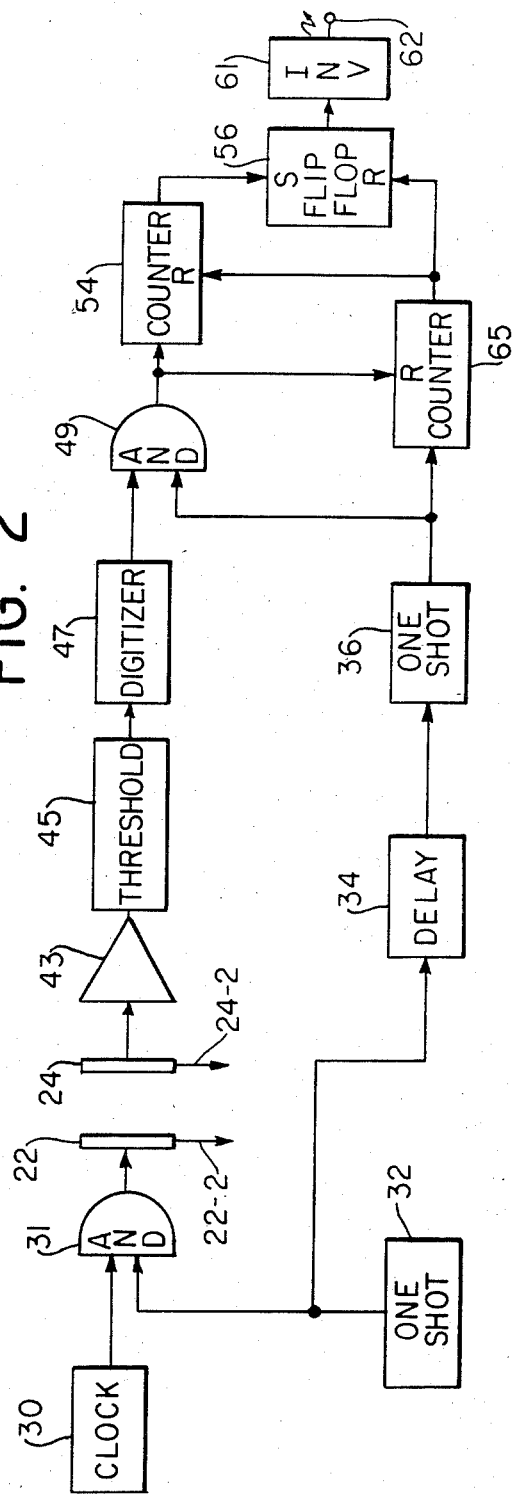
FIG. 2 is a schematic black diagram of a preferred embodiment of the invention.

Referring to FIG. 2, the circuitry of the system includes a clock pulse generator 30 which produces bursts of ultrasonic energy in the form of rectangular clock pulses at a desired frequency, and for a predetermine period of time. Typical frequencies, for the pulses which have been found to work successfully are in the range of about 3 Mhz to about 5 Mhz. Other frequencies can be used depending upon the type of liquid to be sensed, the type of tube, the diameter of the tube, etc. While these frequencies may also be considered to be in the low radio frequency range, they are also considered to be ultrasonic in the sense that they are of higher frequency than sound waves and it is the mechanical properties of the energy which is relied upon for transmission through the liquid rather than the electromagnetic properties. The piezoelectric transducer elements 22, 24 are cut to be resonant at or near the frequency of the pulses from the pulse generator 30.

The clock pulse generator 30 can be on continuously and its pulses are supplied to transducer 22 through an AND gate 31 which is gated open for a predetermined time period by a suitable controller, for example a monostable, self-triggering, one-shot multivibrator circuit 32 which produces an enable signal for a transmit time window. The on time period for the clock pulse generator is from $t_0$ to $t_2$ as shown on line a of FIG. 3 during which the clock pulses are provided to the transducer 22 for transmission through the tube 18. The duration of the transmit window is selected based upon a variety of factors such as minimum bubble size and flow rate. The window time and repetition rate should be such that at least several bursts of energy will pass through a minimum size bubble as it passes across the transducer surface. The clock pulses are shown on line b. It should be understood that many more pulses than those shown are produced during this period.

The one-shot multivibrator 32 is set to have an off period, as shown on line a of FIG. 3 from $t_2$ back to $t_0$ of the next cycle. During each cycle of operation, during the off time of the clock 30, AND gate 31 is closed and no clock pulses are supplied to the transducer 22. During this time, the receiving transducer 24 is available to listen for received signals which are transmitted through the tube and processing of the received signals is taking place.

At the end of the transmit window, when the one-shot 32 changes state, the signal from its output is applied to the input of a triggered delay multivibrator 34 to cause it to change its state. The delay multivibrator 34 produces a predetermined delay inhibit period from $t_2$ to $t_3$ (see line c of FIG. 3) which corresponds to the time it takes to transmit pulses through the tube, i.e. corresponds to the tube diameter or overall width for the frequency of the pulses transmitted. This time is known by virtue of knowledge of the tube diameter, liquid flowing in the tube and pulse frequency.

The output of the delay flip-flop 34, when it changes state, turns on a suitable time control circuit such as a one-shot 36 at $t_3$ to produce a receive window enable signal on line 37 from $t_3$ to $t_4$ (see line d of FIG. 3). That is, when one-shot 36 is in its first state a disable (no receive) signal is produced on its output line 37 and when in a second state as shown on line d an enable (receive signal) is produced on line 37.

Signals received by transducer 24 from transducer 22 which are transmitted through the tube 16 when a liquid is present in the tube are converted from acoustic energy into an analog RF signal by the transducer 24. These signals are applied to the input of an amplifier 43 which can be any conventional analog amplifier, preferably of the wide band type. The output of the amplifier 43 is applied to a threshold detector 45 which operates to pass a signal only above a predetermined threshold level. This prevents noise from entering the remainder of the signal processing circuit. That is, the threshold detector is set above the level of noise in the system so that noise will not trigger the system into producing one type of an indication or another. Line e of FIG. 3 shows the received signal which occurs during the receive window period $t_3$ to $t_4$ if a liquid is present in the tube. If there is an air bubble, then no signal is received.

The output of the threshold detector 45 is applied to a digitizer 47. This is a conventional circuit, which can also include the threshold detector 45, and the digitizer has a pulse shaping, or squaring, circuit. The squaring circuit squares the received signal into pulses which can be processed and counted. The output of the digitizer which is shown on line f of FIG. 3 is applied to a gate, or AND, circuit 49 whose other input is from line 37. The gate 49 is opened only during the receive window period $t_3$ to $t_4$. A valid digitizer output signal which occurs during the receive window period is shown on line g. If an air bubble was in the tube at the time the burst of pulses was transmitted, then there would be no signal received during the receive window period.

It should be understood that the bursts of energy are transmitted at a relatively high rate which corresponds to the flow rate in the tube, that is, there are a large number of bursts transmitted, say four or more, during the time that a single bubble would be passing across the active surface area of the transducers 22, 24. This provides a number of cycles of transmitted and received signals so that signal processing can be performed to ensure a more reliable operation for the system than if merely amplitude level detection were utilized.

The circuit performs signal processing to discriminate against false alarms, i.e. providing a signal that a bubble is present when it is not, or vice versa. This is done by a signal processing technique which produces an output signal indicating the presence of a bubble only after the absence of a received signal through the liquid of the tube has been confirmed for a predetermined number of times. It should be understood that the normal condition for the system is that liquid is flowing through the tube and there are received pulses during the receive window time.

Assuming that there is liquid in the tube 18, the signals received by element 24 are converted to pulses by the digitizer 47 and are passed through the AND gate 49 during the receive window time. These pulses may be provided to a divider-counter (not shown) which would produce an output pulse for a predetermined arbitrary number of input pulses from digitizer. The division ratio would be selected as a function of the frequency of the transmitted signal and the time duration of signal averaging desired. The divider counter may or may not be necessary as determined by such factors as tube diameter.

The output pulses of the digitizer 47 are applied to an overflow type counter 54. This counter is set to produce an output signal after receiving a predetermined number of pulses at its input from digitizer 47. This output signal will be retained for all subsequent input signals until the counter 54 is reset to zero. For example, the overflow count can be that which is equal to the pulses received from the digitizer 47 after there has been a number, say 10 or more, of bursts of energy transmitted through the tube 18. Thus, it takes 10 or more confirmations of the liquid being present in the tube before the overflow counter 54 produces an output signal.

The output signal from overflow counter 54 is applied to the set(S) input of flip-flop 56. When the flip-flop is set, it produces an output signal which is used to control some type of an indicator or a control element, such as a relay (not shown). In a preferred embodiment of the invention, an LED 62 is connected to the flip-flop output through an inverter 61. With this arrangement, the LED will be "off" when there is liquid in the tube and "on" when there is a bubble. If a relay is used, power amplifiers can be located between the flip-flop output and the relay. The relay can be either energized or deenergized in the presence of a liquid or vice versus depending upon the control function to be performed.

Once set, the state of the flip-flop 56 is changed in response to liquid flowing in the tube when a bubble is detected. This is accomplished by a control counter 65, which is also of the overflow type. Counter 65 increments its count by one each time there is a burst of transmitted energy. This is done in response to the firing of the multivibrator 36 which sets the receive window. The control counter 65 has a reset input which is connected to the output of the AND gate 49 which receives the pulses from digitizer 47. The output of control counter 65 is applied to the reset input of the flip-flop 56. If a signal is being received by the transducer 24, indicating that there is liquid flowing in tube 18, then control counter 65 is reset each time digitizer 47 produces an output signal. In this case, the control counter 65 produces no output signal and the state of the flip-flop 64 is left set, i.e., there is liquid in the tube.

If there is no liquid in the tube, that is, there is a bubble, then the digitizer 47 will not produce a reset signal for control counter 65. The count of control counter 65 will now be incremented by one each time there is a burst of energy transmitted and it will continue to increment until its overflow count level is reached. At this time it produces an output signal which resets the flip-flop 56. The count needed to cause control counter 65 to produce an output can be set to a relatively low level, for example, 1, 2, 4, or more. Thus, for example, if the count is set to four, four bursts of pulses which produce no output at the digitizer 47 because there is no liquid, i.e. there is a bubble, will cause the control counter 65 to produce an output signal which will change (to reset) the state of the flip-flop 56. In this case, for example, the LED 62 lights to indicate the presence of a bubble.

When control counter 65 produces an output signal, it is used to reset counter 54 so that it can start to increment from a zero level once the digitizer 47 produces output pulses in response to the re-occurrence of a liquid in the tube. When the bubble passes and the digitizer 47 again starts to produce output pulses, the counter 54 overflows to change the state of flip-flop 56 to the set condition and the LED 62 goes off. The overflow count for counter 54 can be set for any desired number of pulses, say, for example, about half or more of those present during one transmit burst.

It should be noted that if a dry tube is inserted into the sensing head 10 or the counter turned on when there is no tube in the sensing head, the digitizer 47 produces no output pulses, counter 54 does not overflow and the flip-flop 56 is never set. In this case, control counter 65 is not reset and is kept in the overflow state by the signal from multivibrator 36 at each transmit cycle. This keeps flip-flop 56 reset.

If a dry tube is filled with liquid, then the digitizer 47 produces pulses which reset control counter 65 and keep it from incrementing. The flip-flop 56 will temporarily stay in the reset condition, but after a short time the counter 54 will be overflowed so that it produces a signal to set the flip-flop 56 to indicate the presence of a liquid in the tube.

By selecting the number of bursts of no received signals which are needed to trigger the control counter 65, the sensitivity of the detecting system can be set. As previously explained, this is a function of the fluid flow rate through the tube, the rate at which the transmit windows are produced for the clock pulses and other factors. For maximum sensitivity, control counter 65 can be set to produce an output pulse, and thus change the state of the flip-flop, in response to one cycle when no signals are being produced by the digitizer 47.

While the system has been described with respect to detecting air bubbles in a fluid stream, it should be understood that it can also detect solid particles or two different liquids, e.g. drops of slugs of oil or water flowing in a stream of a different liquid, drops of liquid in a gas, etc. As should be apparent, solid particles, the drops of liquid in a gas stream, and a liquid different from the main one have different transmission characteristics to the ultrasonic energy, this will result in different amplitudes of signals being received by the transducer 24. The threshold detector 45 therefore can be set to distinquish between the amplitudes of signals from the two different types of materials flowing in the tube. That is, one level would be passed to the digitizer 47 and the other would not. The ones not passed correspond to the air bubbles are previously described. In the claims that follow, the term discontinuity is used to encompass any such air bubble, particle, different type of liquid, etc.

What is claimed is:

1. Apparatus for detecting a discontinuity in a stream of a first fluid flowing in a tube comprising
  a sensing means having spaced apart transmitting and receiving transducers, the space accommodating the tube,
  means for supplying successive bursts of pulses of electrical energy to said transmitting transducer to cause it to vibrate to produce corresponding bursts of pulses of sonic energy which are transmitted through said tube to said receiving transducer, there being a predetermined time of no pulse production between successive burst of pulses, said receiving transducer converting the bursts of pulses of received sonic energy into corresponding electrical signals during said predetermined time between said successive bursts,
  and circuit means responsive to said electrical signals produced by said receiving transducer during said predetermined time for producing first signals corresponding to the pulses of the transmitted pulses of a burst in response to the presence of said first fluid and a second signal in response to the presence of a discontinuity in said first fluid, and means responsive to receipt of a respective predetermined number of said first or said second signals to produce an output corresponding to the presence of liquid or a discontinuity in said tube.

2. Apparatus as in claim 1 wherein the tube is of compressible material, said sensing means comprising a sensing head with the transducers fixedly mounted thereon with a space therebetween into which the tube fits, the head flattening the tube in the area of said transducers to provide coupling of the sonic energy to and from said tube.

3. Apparatus as in claim 1 wherein said circuit means comprises a threshold detector for producing said first signals in response to the electrical signals above a predetermined amplitude level produced by said receiving transducer corresponding to fluid flowing in the tube.

4. Apparatus as in claim 1 wherein said output producing means comprises first counter means responsive to a predetermined number of said first signals for producing an output indicative of when a fluid is flowing in said tube.

5. Apparatus as in claim 4 wherein said circuit means comprises second counter means responsive to a predetermined number of said second signals a discontinuity in the fluid in the tube.

6. Apparatus as in claim 5 wherein said first counter means resets said second counter means upon receipt of said first signals.

7. Apparatus as in claim 6 wherein said second counter means resets said first counter means upon receipt of a predetermined number of said second signals.

8. Apparatus as in claim 7 further comprising threshold means between said receiving transducer and said first counter means to pass received signals only above a predetermined amplitude.

9. Apparatus as in claim 5 wherein said second counter means resets said first counter means upon receipt of a predetermined number of said second signals.

10. Apparatus as in claim 4 further comprising threshold means between said receiving transducer and said first counter means to pass received signals only above a predetemined amplitude.

11. Apparatus as in claim 1 wherein said output producing means comprises second counter means responsive to a predetermined number of said second signals for producing an output indicative of a discontinuity in the fluid in the tube.

12. Apparatus as in claim 1 wherein said bursts of electrical energy are produced at a rate such that at least one burst of source signals is transmitted through a discontinuity of a given size at a given flow rate of fluid.

13. A method for detecting a discontinuity in a stream of fluid flowing in a tube comprising the steps of:
    placing the tube between a transducer for transmitting sonic energy and one for receiving sonic energy,
    providing said transmitting transducer with successive bursts of pulses to produce corresponding bursts of pulses of sonic energy with a predetermined time interval between successive bursts of pulses,
    detecting receipt of the successive bursts of sonic energy pulses transmitted through said fluid to said receiving transducer and producing during a said predetermined time interval first signals corresponding thereto,
    detecting that a burst of pulses of sonic signals has encountered a discontinuity in the fluid flow and producing a second signal corresponding thereto.

14. A method as in claim 13 further comprising the step of counting a predetermined number of said first signals to validate the presence of a fluid.

15. A method as in claim 13 further comprising the step of counting a predetermined number of said second signals to validate the presence of a discontinuity.

* * * * *